United States Patent
Moldenhauer

(10) Patent No.: US 11,647,714 B2
(45) Date of Patent: May 16, 2023

(54) RICE CULTIVAR 'UADA1701084'

(71) Applicant: THE BOARD OF TRUSTEES OF THE UNIVERSITY OF ARKANSAS, Little Rock, AR (US)

(72) Inventor: Karen A. K. Moldenhauer, Stuttgart, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 11 days.

(21) Appl. No.: 17/061,667

(22) Filed: Oct. 2, 2020

(65) Prior Publication Data

US 2022/0104447 A1 Apr. 7, 2022

(51) Int. Cl.
*A01H 5/10* (2018.01)
*A01H 6/46* (2018.01)

(52) U.S. Cl.
CPC ............. *A01H 6/4636* (2018.05); *A01H 5/10* (2013.01)

(58) Field of Classification Search
None
See application file for complete search history.

(56) References Cited

U.S. PATENT DOCUMENTS

| 6,281,416 | B1 | 8/2001 | Moldenhauer |
| 7,429,697 | B2 * | 9/2008 | Moldenhauer ........... A01H 5/10 800/300 |

* cited by examiner

*Primary Examiner* — Medina A Ibrahim
(74) *Attorney, Agent, or Firm* — Quarles & Brady, LLP

(57) ABSTRACT

A rice cultivar designated UADA1701084 is disclosed herein. The present invention provides seeds, plants, and plant parts derived from rice cultivar UADA1701084. Further, it provides methods for producing a rice plant by crossing UADA1701084 with itself or another rice variety. The invention also encompasses any rice seeds, plants, and plant parts produced by the methods disclosed herein, including those in which additional traits have been transferred into UADA1701084 through the introduction of a transgene or by breeding UADA1701084 with another rice cultivar.

18 Claims, No Drawings

RICE CULTIVAR 'UADA1701084'

BACKGROUND OF THE INVENTION

The present invention relates to a new and distinctive rice cultivar, designated UADA1701084.

Rice is an ancient agricultural crop and is today one of the principal food crops of the world. There are two cultivated species of rice: *Oryza saliva* L., the Asian rice, and *O. glaberrima* Steud., the African rice. *O. saliva* L. constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are preferred rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is provided by irrigation or rainfall. Alternatively, the seed may be broadcast by airplane into a flooded field, which is promptly drained following seeding. With the dry-seeded system, when the plants have reached sufficient size (four- to five-leaf stage), a shallow permanent flood of water, 5 to 16 cm deep, is applied to the field for the remainder of the crop season.

In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders typically employ the production systems predominant in their respective region. Thus, a drill-seeded breeding nursery is used by breeders in a region where rice is drill-seeded and a water-seeded nursery is used in regions where water-seeding is prominent.

Rice in the United States is classified into three primary market types by grain size, shape, and chemical composition of the endosperm: long-grain, medium-grain and short-grain. Typical U.S. long-grain cultivars cook dry and fluffy when steamed or boiled, whereas medium and short-grain cultivars cook moist and sticky. Traditionally, in the southern states, long-grain cultivars have been grown and generally receive higher market prices.

Rice, *Oryza saliva* L., is an important and valuable field crop. A continuing goal of plant breeders is to produce stable, high yielding rice cultivars that are agronomically sound. To accomplish this goal, rice plants with traits that result in superior cultivars must be developed.

SUMMARY OF THE INVENTION

The present invention provides a novel rice cultivar designated UADA1701084. The invention encompasses the seeds, plants, and plant parts of rice cultivar UADA1701084, as well as plants with essentially all of the physiological and morphological characteristics of UADA1701084.

This invention also provides methods for producing a rice plant by planting a plurality of seeds or by crossing rice UADA1701084 with itself or another rice line. Any plant breeding methods using rice cultivar UADA1701084 are part of this invention, including selfing, backcrosses, hybrid production, and crosses to populations. All plants and seeds produced using rice cultivar UADA1701084 as a parent are within the scope of this invention, including gene-converted plants of UADA1701084. Methods for introducing a gene into UADA1701084, either through traditional breeding or transformation, are provided herein.

In still another aspect, the present invention provides regenerable cells for use in tissue culture of rice plant UADA1701084, as well as rice plants regenerated from these tissue cultures.

Definitions

To provide a clear and consistent understanding of the specification and claims, the following definitions are provided:

Apparent starch amylose content. The amount of starch in the endosperm of milled rice that is amylose, provided in g/kg herein. Amylose content varies depending on the growth environment of the rice. It is an important grain characteristic used to describe cooking behavior.

Backcrossing. A process in which a breeder repeatedly crosses hybrid progeny back to a parental line. For example, a first generation ($F_1$) hybrid may be crossed with one of the parental lines used to produce the $F_1$ hybrids.

Breeding. The genetic manipulation of living organisms.

Cell. As used herein, this term includes isolated cells, cells grown in tissue culture, and cells that comprise a plant or plant part.

Cultivar. Used interchangeably with "variety". Refers to plants that are defined by the expression of the characteristics resulting from a given genotype or combination of genotypes, distinguished from any other plant grouping by the expression of at least one characteristic.

Days to 50% heading. The average number of days from emergence to the day when 50% of all panicles are exerted at least partially through the leaf sheath. A measure of maturity.

Embryo. The plant embryo is the part of a seed or bud that contains the earliest forms of the new plant's roots, stem and leaves.

Essentially all of the physiological and morphological characteristics. A plant having "essentially all the physiological and morphological characteristics" of the cultivar exhibits the characteristics of the cultivar with the exception of any characteristics derived from a converted gene.

F #. Denotes a filial generation, wherein the # is the generation number. For example, F1 is the first filial generation.

Gene. Refers to a unit of inheritance corresponding to a distinct sequence of DNA or RNA nucleotides that form part of a chromosome. A gene may encode a polypeptide or a nucleic acid molecule that has a function in the cell or organism.

Gene-converted. Describes a plant wherein essentially all of the desired morphological and physiological characteristics of a parental variety are maintained with the exception of a single trait that was transferred into the variety via backcrossing or genetic engineering.

Genotype. Refers to the genetic constitution of a cell or organism.

Grain yield. Measured in pounds per acre at 12.0% moisture content. The grain yield of rice is determined by the number of panicles per unit area, the number of fertile florets per panicle, and the grain weight per floret.

Haploid. A cell or organism having a single set of unpaired chromosomes.

Head rice. Kernels of milled rice in which greater than ¾ of the kernel is unbroken.

Herbicide resistant. Describes a plant that is tolerant or resistant to an herbicide at a level that would normally kill or inhibit the growth of a normal or wild-type rice plant.

Hybrid. Refers to the offspring or progeny of genetically dissimilar plant parents or stock produced as the result of controlled cross-pollination as opposed to a non-hybrid seed produced as the result of natural pollination.

Kernal length (L). Length of a rice grain, measured in millimeters.

Kernal width (W). Width of a rice grain, measured in millimeters.

Length/width (L/W) ratio. Determined by dividing the average length (L) by the average width (W).

Lodging. The percentage of plant stems that are leaning or have fallen to the ground before harvest. Lodging is determined by visual scoring, in which crops are rated from 0% (all plants standing) to 100% (all plant in plot lying flat on the soil surface). Lodged plants are difficult to harvest and reduce yield and grain quality. Lodging resistance is also called "straw strength".

Milling yield. The total amount of milled rice (whole and broken kernels) recovered after milling (i.e., removal of hulls, bran, and germ). In contrast, head rice yield is the total amount of whole kernels recovered after milling. Both values are expressed as a weight percentage of the original paddy or rough rice sample that was milled. For example, for a sample of 100 grams of rough rice, a milling yield of 65/70 indicates that 65 grams of head rice and 70 grams of total milled rice were produced.

Pedigree. Refers to the lineage or genealogical descent of a plant.

Plant. As used herein, the term "plant" includes plant cells, plant protoplasts, and plant cell tissue cultures from which rice plants can be regenerated; plant calli, plant clumps and plant cells that are intact in plants; and parts of plants, such as embryos, pollen, ovules, flowers, glumes, panicles, leaves, stems, roots, root tips, anthers, and pistils.

Plant height. Measured in centimeters from the soil surface to the tip of the extended panicle at harvest.

Plant parts. Includes, without limitation, protoplasts, leaves, stems, roots, root tips, anthers, pistils, seed, grain, embryo, pollen, ovules, cotyledon, hypocotyl, pod, flower, shoot, tissue, petiole, cells, and meristematic cells.

Progeny. Includes an Ft rice plant produced from the cross of two rice plants, as well as plants produced from subsequent generational crosses (e.g., $F_2$, $F_3$, $F_4$, $F_5$, $F_6$, $F_7$, $F_8$, $F_9$, and $F_{10}$) with the recurrent parental line.

Regeneration. Refers to the development of a plant from tissue culture.

Seeds. Includes seeds and plant propagules of all kinds including, but not limited to, true seeds, seed pieces, suckers, corms, bulbs, fruit, tubers, grains, cuttings, cut shoots and the like. However, in preferred embodiments, it refers to true seeds.

Trait. Refers to an observable and/or measurable characteristic of an organism. For example, the present invention describes plants that have a trait that make them resistant to fluazifop herbicides.

Transgenic. Describes an organism or cell that contains genetic material that has been artificially introduced.

Wild-type. When made in reference to a gene, "wild-type" refers to a functional gene common throughout a plant population and, thus, arbitrarily designated the "normal" or "wild-type" form of the gene.

DETAILED DESCRIPTION OF THE INVENTION

The present invention provides a novel rice cultivar designated UADA1701084. The invention encompasses both the seeds of this cultivar and plants grown from these seeds. The invention further encompasses any rice plant having essentially all of the physiological and morphological characteristics rice cultivar UADA1701084.

As used herein, the term plant includes plant cells, plant protoplasts, plant cell tissue cultures from which rice plants can be regenerated, plant calli, plant clumps and plant cells that are intact in plants or parts of plants, such as embryos, pollen, ovules, flowers, glumes, panicles, leaves, stems, roots, root tips, anthers, pistils, and the like.

Development and Characterization of Rice Cultivar UADA1701084

Rice cultivar UADA1701084 (Poaceae Oryzea *Oryza sativa* L.), is a very high yielding, short season, long-grain rice cultivar. UADA1701084 originated from the cross 'Roy J'/5/'Katy'/'Newbonnet'//'Adair'/3/'Wells'/4/Adair//Katy/Newbonnet/3/'LaGrue' (cross no. 20082431), made in Stuttgart, Ark., in 2008. Roy J (Moldenhauer et al., 2010) is a long-grain lodging resistant high yielding rice. UADA1701084 was bred using hybridization, a combination of modified pedigree and bulk breeding methods, and is adapted to the Southern U.S. rice growing region. The experimental designation for early evaluation of UADA1701084 was STG040L-09-042, starting with a bulk of F8 seed from the 2014 panicle row L-09-042. UADA1701084 was tested in the Arkansas Rice Performance Trials (ARPT) and the Cooperative Uniform Regional Rice Nursery (URRN) during 2017-2019 as entry UADA1701084.

UADA1701084 maturity is between 'Diamond' and Roy J. UADA1701084 has straw strength similar to Diamond. On a relative straw strength scale (0=very strong straw, 9=very weak straw) UADA1701084, Diamond, 'LaKast', and Roy J rated 3, 3, 3, and 1, respectively. UADA1701084 is 104 cm in plant height with an average canopy height of 35 inches which is similar to Diamond and LaKast. UADA1701084 has a lodging resistance similar to Diamond better than that of Wells. The nitrogen fertilizer requirements of UADA1701084 are 135 lbs/a.

Rough rice grain yields of UADA1701084 have consistently ranked as one of the highest in the Arkansas Rice Performance Trials (ARPT). In 14 ARPT tests (2017-2019), UADA1701084, Diamond, LaKast, Roy J, and RT XL753 averaged yields of 206, 205, 189, 193 and 230 bushels/acre, respectively. Data from the URRN conducted at Arkansas during 2017-2019, showed that UADA1701084 average grain yield of 231 bushels/acre compared favorably with those of Diamond, LaKast, and Roy J, at 239, 208, and 199 bushels/acre, respectively. Milling yields (mg $g^{-1}$ whole kernel:mg $g^{-1}$ total milled rice) at 120 mg $g^{-1}$ moisture from the ARPT, 2017-2018, averaged 550:690, 540:690, 550:690, 570:700 and 490:710, for UADA1701084, Diamond, LaKast, Roy J, and RT XL753, respectively. Milling yields for the URRN in Arkansas during the same period of time, 2017-2018, averaged 610:690, 600:690, 600:700 and 620:710, for UADA1701084, Diamond, LaKast, and Roy J, respectively.

UADA1701084 is moderately susceptible to common rice blast (*Pyricularia grisea* (Cooke) Sacc) races IB-1, IB-17, IB-49, IC-17, IE-1, and IE-1K with summary ratings in greenhouse tests of 6, 5, 6, 4, 3 and 4, respectively, using the standard disease scale of 0=immune, 9=maximum disease susceptibility. UADA1701084 is rated MS to sheath blight (*Rhizoctonia solani* Kühn) which compares with Diamond (S), Wells (S), Roy J (MS), and LaKast (MS), using the standard disease R=resistant, MR=moderately resistant, MS=moderately susceptible, S=susceptible and VS=very susceptible to disease. UADA1701084 is rated an S to false smut (*Ustilaginoidea virens* (Cooke) Takah). UADA1701084 is rated S to bacterial panicle blight compared to Diamond (MS) LaKast (MS) and Roy J (MS).

Plants of UADA1701084 have erect culms, dark green erect leaves, and glabrous lemma, palea, and leaf blades. The lemma and palea are straw colored with red-purple apiculi, many of which fade to straw at maturity. Milled kernels of UADA1701084 averaged 6.86 mm compared to Diamond, LaKast, Roy J, and 'CL151' at 7.17, 7.56, 7.31, and 6.87 mm, respectively. Individual milled kernel weights of UADA1701084, Diamond, LaKast, Roy J and CL151 averaged 21.8, 21.84, 22.3, 21.1, and 20.5 mg/kernel, respectively, in the ARPT 2017-2018.

The endosperm of UADA1701084 is nonglutinous, nonaromatic, and covered by a light brown pericarp. Rice quality parameters indicate that UADA1701084 has typical southern U.S. long-grain rice cooking quality characteristics as described by Webb et al. 1985. Data from the Riceland Foods Inc. Quality Laboratory indicate that UADA1701084 has an average apparent starch amylose content of 23.5 g kg$^{-1}$ and an intermediate gelatinization temperature 68.8° C.

The foundation seed field of UADA1701084 was rogued several times throughout the season. The variants that may be found in the release include any combination of the following: taller, shorter, earlier, later, glabrous or pubescent plants as well as intermediate or long-grains and grains with extremely long awns. Other atypical plants may still be encountered in the cultivar. The total variants and/or off-types numbered less than 1 per 5000 plants.

The above-mentioned characteristics of rice cultivar UADA1701084 are based primarily on data collected in Stuttgart, Ark. and are summarized in Table 1. The results of the rice performance trials (ARPT 2017-2019 and URRN 2017-2019) are detailed in the Table 2-13. Tables 14-17 show grain quality and yield data, Tables 18-20 show DD50 program data, Table 21 shows pertinent agronomic information, Table 22 shows nitrogen trial data, and Tables 23-24 show disease evaluation data.

TABLE 1

Cultivar description information

Plant:

Grain type: Long
Days to maturity (Seeding to 50% heading): 90
(range 82-99 days)
Plant height: 100 cm
Plant color (at booting): Dark green
Culm:

Angle (degrees from perpendicular after flowering): Erect
(less than 30°)
Flag leaf (after heading):
Pubescence: Glabrous
Leaf angle (after heading): Erect
Blade color (at heading): Dark green
Panicle:

Length: 22.9 cm
Type: Intermediate
Exertion (near maturity): Moderately well
Axis: Droopy
Shattering (at maturity): Low (1-5%)
Grain (spikelet):

Awns (after full heading): Tip awns at high fertility or
short/long and partly awned
Apiculus color: Red
Stigma color: White
Lemma and palea color (at maturity): Straw
Lemma and palea pubescence: Glabrous
Grain (seed):

Seed coat color: Light brown
Scent: Nonscented
Shape class (length/width ratio):
Paddy: Long (3.4:1 and more)
Brown: Long (3.1:1 and more)
Milled: Long (3.0:1 and more)
Size: 21.8 g/1000 seeds milled rice
Disease resistance:

Rice blast (*Pyricularia grisea* (Cooke) Sacc.): Moderately
susceptible
Sheath blight (*Rhizoctonia solani* Kuhn): Moderately
susceptible
False smut (*Ustilaginoidea virens* (Cooke) Takah.):
Susceptible
Bacterial panicle blight (*Burkholderia glumae* and
*B. gladioli*): Susceptible
Straight head: Moderately resistant

TABLE 2

UADA1701084 data summary from 2017 ARPT. (Stuttgart, RREC; Colt, PTES; Keiser, NEREC; Clay County & Desha County)

| VARIETY | YIELD (BU/AC) | HEIGHT$^a$ (IN.) | HEIGHT$^b$ (IN.) | MATURITY (50% HD) | MILLING HR:TOT |
|---|---|---|---|---|---|
| RU1701081 | 184 | 41 | 37 | 93 | 51:70 |
| UADA1701084 | 210 | 39 | 37 | 93 | 57:69 |
| Jewel | 192 | 41 | 38 | 91 | 59:71 |
| Diamond | 206 | 42 | 38 | 91 | 56:69 |
| LaKast | 188 | 44 | 39 | 89 | 56:70 |

TABLE 2-continued

UADA1701084 data summary from 2017 ARPT. (Stuttgart, RREC;
Colt, PTES; Keiser, NEREC; Clay County & Desha County)

| VARIETY | YIELD (BU/AC) | HEIGHT[a] (IN.) | HEIGHT[b] (IN.) | MATURITY (50% HD) | MILLING HR:TOT |
|---|---|---|---|---|---|
| Roy J | 196 | 42 | 40 | 94 | 60:70 |
| RT XP753 | 220 | 42 | 38 | 87 | 49:70 |

[a] Plant height measured from to the tip of the panicle
[b] Plant height is the canopy height not to tip of panicle

TABLE 3

UADA1701084 data summary from 2018 ARPT (Stuttgart, RREC;
Colt, PTES; Keiser, NEREC; Clay County, & Desha County)

| VARIETY | YIELD (BU/AC) | HEIGHT[a] (IN.) | MATURITY (50% HD) | TEST WEIGHT LBS/BU | MILLING HR:TOT |
|---|---|---|---|---|---|
| RU1701081 | 183 | 36 | 85 | 39.6 | 49:70 |
| UADA1701084 | 201 | 35 | 87 | 40.0 | 54:69 |
| Jewel | 186 | 37 | 85 | 39.9 | 57:70 |
| Diamond | 206 | 36 | 83 | 39.9 | 52:69 |
| LaKast | 187 | 36 | 82 | 40.0 | 53:67 |
| Roy J | 189 | 38 | 90 | 39.4 | 54:69 |
| RTXP753 | 229 | 36 | 80 | 40.4 | 49:71 |

[a] Plant height is the canopy height not to tip of panicle

TABLE 4

UADA1701084 data summary from 2019 ARPT (Stuttgart, RREC;
Colt, PTES; Keiser, NEREC; Clay County and Chicot County)

| VARIETY | YIELD (BU/AC) | HEIGHT (IN.)[a] | MATURITY (50% HD) | TEST WT (lbs/BU) | MILLING HR:TOT* |
|---|---|---|---|---|---|
| RU1701081 | 183 | 35 | 86 | 40.5 | 54:71 |
| UADA1701084 | 206 | 34 | 86 | 40.0 | 56:70 |
| Jewel | 182 | 36 | 85 | 40.0 | 61:71 |
| Diamond | 204 | 35 | 85 | 40.5 | 58:70 |
| LaKast | 193 | 34 | 82 | 41.1 | 58:70 |
| RT XP753 | 242 | 36 | 81 | 40.9 | 56:71 |

[a] Plant height is the canopy height not to tip of panicle

45

TABLE 5

UADA1701084 data summary from 2017-2019 ARPT

| VARIETY | YIELD (BU/AC) | HEIGHT (IN.)[a] | MATURITY (50% HD) | TEST WT (lbs/BU)[c] | MILLING HR:TOT[d] |
|---|---|---|---|---|---|
| RU1701081 | 183 | 36 | 88 | 40.1 | 51:70 |
| UADA1701084 | 206 | 35 | 89 | 40.0 | 55:69 |
| Jewel | 187 | 37 | 87 | 40.0 | 59:71 |
| Diamond | 205 | 36 | 86 | 40.2 | 56:69 |
| LaKast | 189 | 36 | 84 | 40.6 | 56:69 |
| Roy J[b] | 193 | 39 | 92 | — | 57:70 |
| RT XP753 | 230 | 37 | 83 | 40.6 | 51:71 |

[a] Plant height is the canopy height not to tip of panicle
[b] 2107 & 2018 data
[c] test weight from 2018 & 2019
[d] 2017 & 2018 data

TABLE 6

2017 ARPT mean by location (Stuttgart, RREC; Colt, PTES; Keiser, NEREC; Clay County and Desha County)

| VARIETY | 2017 GRAIN YIELD (BU/AC) | | | | | | HEAD RICE(%):TOTAL RICE(%) | | | | | |
|---|---|---|---|---|---|---|---|---|---|---|---|---|
|  | RREC | NEREC | PTES | CLAY | CHICOT | AVG | RREC | NEREC | PTES | CLAY | CHICOT | AVG |
| RU1701081 | 183 | 192 | 163 | 197 | 184 | 184 | 61:72 | 57:70 | 47:69 | 53:72 | 37:69 | 51:70 |
| UADA1701084 | 201 | 205 | 201 | 229 | 217 | 210 | 59:70 | 61:68 | 54:67 | 61:70 | 50:68 | 57:69 |
| Jewel | 203 | 192 | 169 | 205 | 190 | 192 | 61:73 | 60:70 | 61:71 | 60:71 | 50:70 | 59:71 |
| Diamond | 214 | 204 | 177 | 227 | 208 | 206 | 60:68 | 61:71 | 60:69 | 61:71 | 43:68 | 56:69 |
| LaKast | 194 | 179 | 172 | 201 | 197 | 188 | 57:69 | 60:72 | 58:70 | 61:71 | 44:70 | 56:70 |
| Roy J | 197 | 205 | 184 | 209 | 186 | 196 | 61:69 | 65:72 | 60:69 | 65:72 | 50:70 | 60:70 |
| RT XP 753 | 231 | 222 | 201 | 230 | 214 | 220 | 59:71 | 57:70 | 51:68 | 48:70 | 32:69 | 49:70 |

TABLE 7

2018 ARPT mean by location (Stuttgart, RREC; Colt, PTES; Keiser, NEREC; Clay County and Chicot County)

| VARIETY | 2018 GRAIN YIELD (BU/AC) | | | | | | HEAD RICE(%):TOTAL RICE(%) | | | | | |
|---|---|---|---|---|---|---|---|---|---|---|---|---|
|  | RREC | NEREC | PTES | CLAY | CHICOT | AVG | RREC | NEREC | PTES | CLAY | CHICOT | AVG |
| RU1701081 | 182 | 154 | 186 | 199 | 192 | 183 | 60:70 | 38:69 | 48:70 | 42:72 | 59:70 | 49:70 |
| UADA1701084 | 204 | 198 | 204 | 196 | 201 | 201 | 60:68 | 50:68 | 52:69 | 50:71 | 58:69 | 54:69 |
| Jewel | 183 | 157 | 183 | 204 | 202 | 186 | 58:69 | 53:68 | 57:70 | 59:72 | 59:71 | 57:70 |
| Diamond | 204 | 189 | 195 | 228 | 213 | 206 | 57:68 | 50:68 | 51:69 | 48:72 | 57:70 | 52:69 |
| LaKast | 191 | 161 | 190 | 213 | 181 | 187 | 58:70 | 42:54 | 52:70 | 54:72 | 58:71 | 53:67 |
| RoyJ | 193 | 178 | 190 | 204 | 178 | 189 | 52:66 | 55:69 | 54:70 | 50:72 | 58:71 | 54:69 |
| RT XP 753 | 252 | 165 | 232 | 261 | 234 | 229 | 62:71 | 36:69 | 51:70 | 37:73 | 60:72 | 49:71 |

TABLE 8

2019 ARPT mean by location (Stuttgart, RREC; Colt, PTES; Keiser, NEREC; and Clay County)

| VARIETY | GRAIN YIELD (BU/AC) | | | | | HEAD RICE(%):TOTAL RICE(%) | | | | |
|---|---|---|---|---|---|---|---|---|---|---|
|  | RREC | NEREC | PTES | CLAY | AVG | RREC | NEREC | PTES | CLAY | AVG |
| RU1701081 | 215 | 179 | 148 | 191 | 183 | 56:70 | 64:71 | 35:70 | 62:72 | 54:71 |
| UADA1701084 | 225 | 197 | 179 | 222 | 206 | 56:68 | 65:70 | 40:69 | 64:71 | 56:70 |
| Jewel | 211 | 171 | 156 | 189 | 182 | 57:69 | 60:68 | 61:72 | 64:72 | 61:71 |
| Diamond | 219 | 193 | 179 | 226 | 204 | 55:68 | 62:69 | 52:70 | 63:72 | 58:70 |
| LaKast | 213 | 202 | 161 | 203 | 195 | 57:70 | 60:69 | 49:70 | 64:72 | 58:70 |
| RT XP753 | 265 | 245 | 201 | 256 | 242 | 60:71 | 62:72 | 40-:70 | 63:73 | 56:71 |

TABLE 9

2017-2019 ARPT mean by location (Stuttgart, RREC; Colt, PTES; Keiser, NEREC; Clay County and Desha/Chicot County)

| VARIETY | GRAIN YIELD (BU/AC) | | | | | | HEAD RICE(%):TOTAL RICE(%)[a] | | | | | |
|---|---|---|---|---|---|---|---|---|---|---|---|---|
|  | RREC | NEREC | PTES | CLAY | CHICOT | AVG | RREC | NEREC | PTES | CLAY | CHICOT | AVG |
| RU1701081 | 193 | 175 | 166 | 196 | 188 | 183 | 61:71 | 48:70 | 48:70 | 48:72 | 48:70 | 51:71 |
| UADA1701084 | 210 | 200 | 195 | 216 | 209 | 206 | 60:69 | 56:68 | 53:68 | 56:71 | 54:69 | 56:69 |
| Jewel | 199 | 173 | 169 | 199 | 196 | 187 | 60:71 | 57:69 | 59:71 | 60:72 | 55:71 | 58:71 |
| Diamond | 212 | 195 | 184 | 227 | 211 | 205 | 59:68 | 56:70 | 56:69 | 55:72 | 50:69 | 55:70 |
| LaKast | 199 | 181 | 174 | 206 | 189 | 190 | 58:70 | 51:63 | 55:70 | 58:72 | 51:71 | 55:69 |
| Roy J[a] | 195 | 192 | 187 | 206 | 182 | 192 | 57:68 | 60:71 | 57:70 | 58:72 | 54:71 | 57:70 |

[a]2017-2018 data

TABLE 10

2017 Arkansas URN data

| VARIETY | YIELD (BU/AC) | HEIGHT (IN.) | MATURITY (50% HD) | MILLING HR:TOT |
|---|---|---|---|---|
| RU1701081 | 219 | 43 | 84 | 59:69 |
| UADA1701084 | 238 | 42 | 83 | 60:69 |
| Jewel | 224 | 46 | 82 | 60:69 |
| Diamond | 245 | 43 | 82 | 58:68 |
| LaKast | 201 | 46 | 80 | 56:69 |
| Roy J | 211 | 46 | 87 | 60:69 |

TABLE 11

2018 Arkansas URN data

| VARIETY | YIELD (BU/AC) | HEIGHT (IN.) | MATURITY (50% HD) | MILLING HR:TOT |
|---|---|---|---|---|
| RU1701081 | 230 | 42 | 81 | 59:71 |
| UADA1701084 | 220 | 41 | 83 | 62:69 |
| Jewel | 218 | 45 | 79 | 59:69 |
| Diamond | 219 | 45 | 80 | 62:70 |
| LaKast | 215 | 47 | 76 | 63:71 |
| Roy J | 187 | 45 | 85 | 64:72 |

TABLE 12

2019 Arkansas URN data

| VARIETY | YIELD (BU/AC) | HEIGHT (IN.) | MATURITY (50% HD) | MILLING HR:TOT |
|---|---|---|---|---|
| RU1701081 | 228 | 45 | 91 | 65:73 |
| UADA1701084 | 234 | 41 | 93 | 59:73 |
| Jewel | 245 | 43 | 90 | 63:72 |
| Diamond | 253 | 44 | 89 | 59:72 |
| Roy J | 202 | 45 | 95 | 56:72 |

TABLE 13

2017-2019 Arkansas URN data

| VARIETY[a] | YIELD (BU/AC) | HEIGHT (IN.) | MATURITY (50% HD) | MILLING HR:TOT[b] |
|---|---|---|---|---|
| RU1701081 | 226 | 43 | 85 | 59:70 |
| UADA1701084 | 231 | 41 | 86 | 61:69 |
| Jewel | 229 | 45 | 84 | 60:69 |
| Diamond | 239 | 44 | 84 | 60:69 |
| LaKast | 208 | 47 | 78 | 60:70 |
| Roy J | 199 | 46 | 86 | 62:71 |

[a]LaKast and Roy J are only from 2017 & 2018 not included in 2019 test. Maturity may not be comparable for the LaKast and Roy J Milling from 2017 and 2018 for all entries

TABLE 14

2017-2018 quality data obtained from the Riceland Laboratory.

| Cultivar | Milling Data | | | | Satake | | Moisture (%) | Chalk (%) | Length (mm) | Width (mm) | Thickness (mm) | L:W Ratio |
| | Head Yield | Total Yield | Hull Yield | Bran Yield | Whiteness | Milling Degree | | | | | | |
|---|---|---|---|---|---|---|---|---|---|---|---|---|
| Diamond | 64.7 | 69.9 | 17.7 | 12.4 | 41.0 | 96.1 | 9.1 | 1.41 | 7.17 | 2.12 | 1.74 | 3.4 |
| LaKast | 64.8 | 70.2 | 17.7 | 12.0 | 43.4 | 108.3 | 9.1 | 1.27 | 7.56 | 2.11 | 1.73 | 3.6 |
| Roy J | 64.6 | 69.9 | 17.7 | 12.4 | 40.7 | 96.4 | 9.4 | 1.09 | 7.31 | 2.08 | 1.74 | 3.5 |
| Jewel | 62.8 | 69.9 | 17.1 | 13.0 | 41.9 | 99.6 | 9.3 | 1.29 | 7.13 | 2.16 | 1.67 | 3.3 |
| UADA1701084 | 64.9 | 69.8 | 18.2 | 12.1 | 39.0 | 86.4 | 9.4 | 2.53 | 6.86 | 2.22 | 1.77 | 3.1 |
| RU1701087 | 64.3 | 69.2 | 17.3 | 13.5 | 40.8 | 96.6 | 9.2 | 1.41 | 7.07 | 2.10 | 1.67 | 3.4 |
| CL151 | 64.7 | 69.6 | 17.9 | 12.5 | 38.8 | 91.5 | 8.9 | 2.51 | 6.87 | 2.22 | 1.69 | 3.1 |

*The data are averages of the ARPT locations is a given year (2017 and 2018 five locations: Rice Research and Extension Center (RREC), Stuttgart, AR; Pine Tree Experiment Station (PTES) Colt, AR; Northeast Research and Extension Center, Keiser (NEREC), AR; Producer Field, Clay County (CLCO), AR; Producer Field, and Chicot County (CCO), AR

TABLE 15

2017-2018 kernel characteristics.

| Cultivar | Weight (g) | Gel Temp (° C.) | Amylose (%) | RVA (rvu) | | | | |
| | | | | Peak | Trough | Breakdown | Final | Setback |
|---|---|---|---|---|---|---|---|---|
| Diamond | 21.4 | 69.3 | 23.7 | 263 | 134 | 129 | 271 | 8 |
| LaKast | 22.3 | 68.7 | 23.9 | 270 | 148 | 121 | 288 | 18 |
| Roy J | 21.1 | 68.8 | 24.2 | 259 | 132 | 126 | 268 | 9 |
| RU1701081 | 21.0 | 69.3 | 23.1 | 256 | 139 | 116 | 275 | 19 |
| UADA1701084 | 21.8 | 68.8 | 23.5 | 250 | 129 | 121 | 264 | 13 |
| Jewel | 19.9 | 70.7 | 25.6 | 192 | 101 | 91 | 220 | 27 |
| CL151 | 20.5 | 70.4 | 23.3 | 264 | 141 | 123 | 279 | 16 |

*The data are averages of the ARPT locations is a given year (2017 and 2018 five locations: Rice Research and Extension Center (RREC), Stuttgart, AR; Pine Tree Experiment Station (PTES) Colt, AR; Northeast Research and Extension Center, Keiser (NEREC), AR; Producer Field, Clay County (CLCO), AR; Producer Field, and Chicot County (CCO), AR

TABLE 16

2018 Producer Rice Evaluation Program results: grain yield bushels/acre

| Cultivar | Grain Type | Craighead | Crittenden | Lonoke | Perry | Poinsett | Prairie | Randolph | St. Francis | White | Woodruff | AVG Grain Yield |
|---|---|---|---|---|---|---|---|---|---|---|---|---|
| Diamond | L | 197 | 245 | 210 | 220 | 167 | 185 | 198 | 190 | 207 | 199 | 202 |
| LaKast | L | 219 | 230 | 192 | 199 | 155 | 208 | 201 | 176 | 196 | 214 | 199 |
| Roy J | L | 206 | 260 | 209 | 212 | 146 | 183 | 183 | 179 | 205 | 191 | 197 |
| 'Titan' | M | 228 | 230 | 194 | 223 | 170 | 216 | 203 | 184 | 237 | 228 | 211 |
| 'Jupiter' | M | 181 | 238 | 193 | 232 | 155 | 183 | 193 | 176 | 228 | 222 | 200 |
| RT XP753 | L | 256 | 280 | 258 | 262 | 191 | 218 | 219 | 210 | 239 | 270 | 240 |
| UADA1701084 | L | 203 | 216 | 213 | 174 | 161 | 188 | 194 | 177 | 200 | 204 | 193 |
| Mean | | 213 | 243 | 210 | 217 | 164 | 197 | 199 | 185 | 216 | 218 | 206 |

TABLE 17

2018 Producer Rice Evaluation Program results: milling yields

| Cultivar | Grain Type | Craighead | Crittenden | Lonoke | Perry | Poinsett | Prairie | Randolph | St. Francis | White | Woodruff | AVG Milling |
|---|---|---|---|---|---|---|---|---|---|---|---|---|
| Diamond | L | 52-69 | 59-71 | 59-70 | 48-68 | 47-69 | 57-70 | 38-72 | 51-70 | 61-72 | 57-68 | 53-70 |
| LaKast | L | 53-70 | 63-73 | 59-72 | 49-69 | 47-70 | 58-71 | 43-71 | 57-71 | 63-72 | 59-71 | 55-71 |
| Roy J | L | 55-71 | 64-73 | 57-71 | 52-70 | 47-70 | 56-70 | 41-71 | 56-71 | 62-73 | 55-69 | 55-71 |
| Titan | M | 62-70 | 59-71 | 60-70 | 36-67 | 38-69 | 52-70 | 22-71 | 47-70 | 66-72 | 63-71 | 50-70 |
| Jupiter | M | 63-69 | 68-72 | 66-70 | 45-68 | 50-69 | 38-69 | 34-70 | 38-69 | 65-70 | 59-69 | 53-69 |
| RT XP753 | L | 56-71 | 62-74 | 61-73 | 48-71 | 40-71 | 58-72 | 31-72 | 47-70 | 61-73 | 61-72 | 52-72 |
| UADA1701084 | L | 57-70 | 63-72 | 59-69 | 45-68 | 43-70 | 58-70 | 31-70 | 54-71 | 60-70 | 59-69 | 53-70 |
| Mean | | 56-70 | 62-72 | 60-70 | 48-69 | 45-70 | 56-70 | 36-71 | 51-70 | 62-72 | 60-70 | 54-70 |

TABLE 18

DD50 milling yield 2018

| | % HR-TR | | | | | | |
|---|---|---|---|---|---|---|---|
| Cultivar | 22-Mar | 5-Apr | 19-Apr | 2-May | 15-May | 5-Jun | Average |
| UADA1701084 | 54-67 | 53-66 | 54-67 | 53-66 | 53-67 | 65-71 | 55-68 |
| Diamond | 54-68 | 52-68 | 52-68 | 53-67 | 55-67 | 61-70 | 55-68 |
| Jupiter | 58-67 | 60-66 | 60-66 | 59-66 | 56-65 | 53-67 | 58-66 |
| LaKast | 54-68 | 53-67 | 53-67 | 52-68 | 51-67 | 63-71 | 54-68 |
| RoyJ | 55-69 | 52-67 | 54-68 | 52-67 | 55-67 | 63-71 | 55-68 |
| RT XP753 | 56-69 | 56-68 | 54-68 | 55-69 | 51-67 | 63-71 | 56-69 |
| Titan | 57-68 | 59-66 | 59-67 | 60-67 | 51-66 | 58-69 | 57-67 |
| Wells | 55-69 | 52-68 | 48-67 | 49-68 | 51-69 | 63-72 | 53-69 |
| Mean | 56-68 | 56-67 | 55-67 | 55-67 | 53-67 | 61-70 | 56-68 |

*The DD50 program was developed in the 1970's to help rice farmers accurately time mid-season nitrogen applications. The DD50 is a modification of the growing degree-day concept, which uses temperature data to predict rice development.

TABLE 19

2018 DD50 Summary Tables

| Seeding | 21-Mar | | 83 | 5-Apr | | 19-Apr | | 2-May | | 15-May | | 5-Jun | | Average | |
|---|---|---|---|---|---|---|---|---|---|---|---|---|---|---|---|
| Emergence | 23-Apr | | 103 | 2-May | | 4-May | | 10-May | | 21-May | | 13-Jun | | | |
| Flood | 1-Jun | | 126 | 1-Jun | | 7-Jun | | 7-Jun | | 13-Jun | | 3-Jul | | | |

| Timing | DAYS | DD50 UNITS | DAYS | DD50 UNITS | DAYS | DD50 UNITS | DAYS | DD50 UNITS | DAYS | DD50 UNITS | DAYS | DD50 UNITS | DAYS | DD50 UNITS |
|---|---|---|---|---|---|---|---|---|---|---|---|---|---|---|
| Days from seeding to emergence | 33 | 229 | 27 | 227 | 15 | 199 | 8 | 199 | 6 | 174 | 8 | 244 | 16 | 212 |

TABLE 19-continued

2018 DD50 Summary Tables

| | | | | | | | | | | | | | |
|---|---|---|---|---|---|---|---|---|---|---|---|---|---|
| Days from emergence to flooding | 39 | 963 | 30 | 848 | 34 | 957 | 28 | 812 | 23 | 673 | 20 | 621 | 29 | 812 |
| Days from seeding to flooding | 72 | 1421 | 57 | 1075 | 49 | 1156 | 36 | 1011 | 29 | 847 | 28 | 865 | 45 | 1062 |

TABLE 20

DD50 information for UADA1701084 - 2018

50% Heading

| | 22 Mar. 2018 | | 5 Apr. 2018 | | 19 Apr. 2018 | | 2 May 2018 | | 15 May 2018 | | 5 Jun. 2018 | | Average | |
|---|---|---|---|---|---|---|---|---|---|---|---|---|---|---|
| Cultivar | DAYS | DD50 UNITS | DAYS | DD50 UNITS | DAYS | DD50 UNITS | DAYS | DD50 UNITS | DAYS | DD50 UNITS | DAYS | DD50 UNITS | DAYS | DD50 UNITS |
| AREX7-1084 | 87 | 2421 | 81 | 2405 | 84 | 2496 | 80 | 2404 | 80 | 2392 | 76 | 2266 | 81 | 2397 |
| Diamond | 85 | 2374 | 75 | 2222 | 69 | 2093 | 73 | 2199 | 69 | 2052 | 85 | 2374 | 76 | 2219 |
| Jupiter | 79 | 2336 | 75 | 2262 | 73 | 2202 | 75 | 2243 | 83 | 2444 | 78 | 2308 | 77 | 2299 |
| LaKast | 78 | 2308 | 80 | 2387 | 78 | 2344 | 75 | 2236 | 78 | 2286 | 83 | 2345 | 79 | 2318 |
| RoyJ | 81 | 2418 | 81 | 2432 | 77 | 2325 | 76 | 2276 | 79 | 2302 | 86 | 2453 | 80 | 2368 |
| RT XP753 | 76 | 2267 | 75 | 2239 | 74 | 2238 | 71 | 2116 | 82 | 2316 | 78 | 2288 | 76 | 2244 |
| Titan | 75 | 2235 | 71 | 2129 | 76 | 2284 | 69 | 2068 | 81 | 2292 | 79 | 2296 | 75 | 2217 |
| Wells | 80 | 2378 | 77 | 2330 | 79 | 2361 | 75 | 2223 | 83 | 2339 | 76 | 2230 | 78 | 2310 |
| Mean | 82 | 2349 | 78 | 2326 | 79 | 2356 | 76 | 2271 | 78 | 2304 | 77 | 2263 | 78 | 2311 |
| C.V | 0.59 | 0.67 | 1.65 | 2.10 | 2.80 | 2.85 | 3.09 | 2.90 | 3.03 | 4.98 | 3.55 | 3.86 | 5.89 | 4.75 |
| LSD | 0.7 | 22.5 | 1.8 | 67.8 | 3.2 | 96.9 | 3.4 | 97.4 | 3.3 | 162.4 | 3.7 | 119.4 | 2.6 | 62.4 |

TABLE 21

Pertinent agronomic information for the Northeast Research and Extension Center (NEREC), Pine Tree Research Station (PTRS), and the Rice Research and Extension Center (RREC) during 2015.

| PRACTICES | NEREC | PTRS** | RREC |
|---|---|---|---|
| Pre-plant Fertilizer | | | 0-60-90 + 10 lbs Zn as ZnSO4 |
| Planting Dates | 5/4 | 6/5 | 5/1 |
| Herbicide Spray Dates and Spray Procedures | 5/6 40 oz/acre Facet L + 1.3 pt/acre Command + 0.75 oz/acre Permit Plus + 32 oz/acre RoundUp | 6/5 1.0 pt/acre Command + 0.75 oz/acre Permit Plus | 5/1 20 oz/acre Obey |
| Flush Dates | | | |
| Emergence Dates | 5/20 | 6/11 | 5/10 |
| Herbicide Spray Dates and Spray Procedures | 6/11 4 qt/acre Stam + 1 pt/acre Grandstand | 6/16 3 qt/acre Riceshot + 32 oz/acre Facet L | 6/1 2 qt Prowl + 0.75 oz/acre Permit Plus |
| Herbicide Spray Dates and Spray Procedures | | 6/23 32 oz/acre Facet L + 1 pt/acre Bolero | |
| Herbicide Spray Dates and Spray Procedures | | | |
| Preflood N Dates | 6/18 | 6/24 | 6/3 |
| Flood Dates | 6/19 | 6/25 | 6/4 |
| Drain Dates | 9/9 | 10/1 | 8/28 |
| Harvest Dates | 9/23 | 10/14 | 9/2 |

**Zinc EDTA applied (7/10)

TABLE 22

Influence of nitrogen (N) fertilizer rate on the grain yield of UADA1701084 rice at three locations during 2019.

| N Fertilizer Rate (lbs N/A) | Grain Yield | | |
|---|---|---|---|
| | NEREC[a] | PTRS (bushels/acre) | RREC |
| 0 | 85 | 72 | 125 |
| 60 | — | 128 | 170 |
| 90 | 172 | 149 | 203 |
| 120 | 167 | 159 | 219 |
| 150 | 179 | 164 | 235 |
| 180 | 191 | 174 | 234 |
| 210 | 188 | — | — |

[a]NEREC = Northeast Research and Extension Center, Keiser, AR; PTRS = Pine Tree Research Station, Colt, AR; RREC = Rice Research and Extension Center, Stuttgart, AR.
[b]LSD = least significant difference, C. V. = coefficient of variation.

Disease Evaluations of Rice Cultivar UADA1701084

Varietal resistance is the most efficient and reliable means of controlling rice diseases. Conservation and improvement of disease resistance is a continuous endeavor basic to varietal development. Incorporation of existing and new resistance sources is a complex process limited by several variables. The rice disease research program routinely evaluates breeding program entries to provide disease data required for superior variety development. Our objectives are to increase varietal disease resistance and to define disease liabilities of new varieties released for rice production in Arkansas.

Rice diseases are mostly rated visually on a 0-9 scale to estimate degree of severity. Numerical data is often converted to this scale. A rating of zero indicates complete disease immunity. A rating of one to three indicates resistance where little loss occurs and in the case of rice blast pathogen growth is restricted considerably. Conversely, a nine rating indicates maximum disease susceptibility, which typically results in near complete plant death and/or yield loss. Depending upon the disease in question, a disease rating of four to six is usually indicative of acceptable disease resistance under conditions slightly favoring the pathogen. Numerical ratings are sometimes converted to letter symbols where 0-3=R (resistant), 3-4=MR (moderately resistant), 5-6=MS (moderately susceptible) 7=S (susceptible) and 8-9 VS (very susceptible). Exceptions to established ratings do occur unexpectedly as disease situations change.

These data come from several sources. Advanced and promising breeding lines are normally evaluated by researchers in other states. It is not unusual for ratings to vary with location and year due to environmental differences and research procedures. Ratings within a source traditionally have been consistent.

Greenhouse blast tests are the primary means of screening large number of entries for varietal reaction to the many blast races occurring in the production areas. Although results are quite variable and testing conditions tend to overwhelm any field resistance present in the entry, this test provides an accurate definition of the fungus-variety genetics. Blast field nurseries, utilizing both natural and lab produced inoculum, are established in an effort to better define blast susceptibility under field conditions.

Field nurseries are established and artificially inoculated to provide a uniform disease pressure for evaluations under field conditions. Grower nurseries are established and operate in an effort to evaluate disease reactions in grower fields under current production practices. Over time these nurseries document variety performance under adverse disease conditions in Arkansas production fields.

Below, Tables 23-24 show disease evaluation data.

TABLE 23

Summary of available leaf blast rating data from UADA1701084 plants inoculated with the indicated race using standard greenhouse techniques.

| Year | IB-1 | IB-17 | IB-49 | IC-17 | IE-1K | IE-1 |
|---|---|---|---|---|---|---|
| 2019 | 6 | 5 | 6 | 4 | 4 | N/A |
| 2017 | 5, 4 | 5 | 3, 4, 5 | 4, 5 | 0, 0, 0, 4 | 3, 0 |

TABLE 24

Rice variety reactions[1] to diseases (2018-19).

| Cultivar | Sheath Blight | Blast | Straighthead | Bacterial Panicle Blight | Narrow Brown Leaf Spot | Stem Rot | Kernel Smut | False Smut | Lodging | Black Sheath Rot |
|---|---|---|---|---|---|---|---|---|---|---|
| UADA1701084 | MS | S | MR | S | MS | | | S | | |
| Diamond | S | S | | MS | | S | S | VS | MS | |
| LaKast | MS | S | MS | MS | MS | S | S | S | MS | MS |
| Roy J | MS | S | S | S | R | S | VS | S | MR | MS |
| RiceTec XL753 | MS | R | MS | MR | R | | MS | S | MS | S |
| RiceTec XP760 | MS | MR | | MR | R | | MS | VS | S | |
| Wells | S | S | S | S | S | VS | S | S | MS | MS |

[1]Reaction: R = Resistant; MR = Moderately Resistant; MS = Moderately Susceptible; S = Susceptible; VS = Very Susceptible. Reactions were determined based on historical and recent observations from test plots and in grower fields across Arkansas. In general, these reactions would be expected under conditions that favor severe disease development including excessive nitrogen rates (most diseases) or low flood depth (blast).

Methods

This present invention provides methods for producing rice plants. In some embodiments, these methods involve crossing a first parent rice plant with a second parent rice plant wherein either the first or second parent rice plant is a rice plant of the line UADA1701084. Further, both first and second parent rice plants can come from the rice cultivar UADA1701084. Still further, this invention also is directed to methods for producing a rice cultivar UADA1701084-derived rice plant by crossing rice cultivar UADA1701084 with a second rice plant and growing the progeny seed, and repeating the crossing and growing steps with the rice cultivar UADA1701084-derived plant from 0 to 7 times. Thus, any such methods using the rice cultivar UADA1701084 are part of this invention: selfing, backcrosses, hybrid production, crosses to populations, and the like. All plants produced using rice cultivar UADA1701084 as a parent are within the scope of this invention, including plants derived from rice cultivar UADA1701084. Advantageously, the rice cultivar is used in crosses with other, different, rice cultivars to produce first generation ($F_1$) rice seeds and plants with superior characteristics.

In some embodiments, a UADA1701084 progeny plant is selected that has molecular markers, morphological characteristics, and/or physiological characteristics in common with UADA1701084 (e.g., those listed in Table 1). Techniques such as RFLP-enhanced selection, genetic marker enhanced selection (e.g., SSR markers), and the making of double haploids may be utilized to identify progeny that share particular traits with UADA1701084.

Further, this invention provides methods for introducing a desired trait into rice cultivar UADA1701084. This may be accomplished using traditional breeding methods, such as backcrossing (see Breeding Methods section below). Alternatively, the desired trait may be introduced by transforming the rice cultivar with a transgene (see Transformation Methods section below). The transgenic cultivar produced by these methods may be crossed with another cultivar to produce a new transgenic cultivar. Alternatively, the transgene incorporated by these methods could be moved into another cultivar using traditional backcrossing techniques.

Optionally, any of the disclosed methods may further comprise additional steps involving producing rice seed from the resulting rice plants and/or planting the rice seed.

The present invention encompasses all plants, or parts thereof, produced by the methods described herein, as well as the seeds produced by these plants. Further, any plants derived from rice cultivar UADA1701084 or produced from a cross using cultivar UADA1701084 are provided. This includes genetic variants, created either through traditional breeding methods or through transformation, as well as plants produced in a male-sterile form. Notably, this includes gene-converted plants developed by backcrossing. Any of the seeds, plants, or plant parts provided may be utilized for human food, livestock feed, and as a raw material in industry.

The present invention also encompasses progeny of rice cultivar UADA1701084 comprising a combination of at least two UADA1701084 traits selected from those listed in the Tables and Detailed Description of the Invention, wherein the progeny rice plant is not significantly different from UADA1701084 for said traits, as determined at the 5% significance level when grown in the same environment. One of skill in the art knows how to compare a trait between two plant varieties to determine if there is a significant difference between them (Fehr and Walt, Principles of Cultivar Development, pp. 261-286 (1987)). Molecular markers or mean trait values may be used to identify a plant as progeny of UADA1701084. Alternatively, progeny may be identified through their filial relationship with rice cultivar UADA1701084 (e.g., as being within a certain number of breeding crosses of rice cultivar UADA1701084). For example, progeny produced by the methods described herein may be within 1, 2, 3, 4, or 5 breeding crosses of rice cultivar UADA1701084.

Tissue Culture

The present invention provides tissue cultures of regenerable cells or protoplasts produced from rice cultivar UADA1701084. As is well known in the art, tissue culture of rice can be used for the in vitro regeneration of a rice plant. Thus, such cells and protoplasts may be used to produce plants having the physiological and morphological characteristics of rice variety UADA1701084. The rice plants regenerated by these methods are also encompassed by the present invention.

As used herein, the term "tissue culture" describes a composition comprising isolated cells or a collection of such cells organized into parts of a plant. Exemplary tissues for culture include protoplasts, calli, plant clumps, and plant cells that can be grown in culture, or parts of plants, such as embryos, pollen, flowers, seeds, pods, leaves, stems, roots, root tips, and anthers. Culture of various rice tissues and regeneration of plants therefrom is well known in the art.

Breeding Methods

The goal of rice breeding is to develop new, superior rice cultivars and hybrids. A superior cultivar is produced when a new combination of desirable traits is formed within a single plant variety. Desirable traits may include higher seed yield, resistance to diseases and insects, better stems and roots, tolerance to low or high temperatures, herbicide resistance, and better agronomic characteristics or grain quality.

The breeding methods used with the present invention may involve a single-seed descent procedure, in which one seed per plant is harvested and used to plant the next generation. Alternatively, the methods may utilize a multiple-seed procedure, in which one or more seeds harvested from each plant in a population is threshed together to form a bulk which is used to plant the next generation.

Use of rice cultivar UADA1701084 in any plant breeding method is encompassed by the present invention. The choice of a breeding or selection method will depend on several factors, including the mode of plant reproduction, the heritability of the trait(s) being improved, and the type of cultivar used commercially (e.g., F1 hybrid cultivar, pureline cultivar). Popular selection methods include pedigree selection, modified pedigree selection, mass selection, recurrent selection, backcrossing, or a combination thereof.

Pedigree selection is commonly used for the improvement of self-pollinating crops. Two parents are crossed to produce an $F_1$ population. An $F_2$ population is produced by selfing one or several $F_1$'s. Selection of the best individuals may begin in the $F_2$ population; then, beginning in the $F_3$ generation, the best individuals in the best families are selected. Replicative testing of families can begin in the Fa generation to make selection of traits with low heritability more effective. At an advanced stage of inbreeding (e.g., $F_6$ or $F_7$), the best lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population, which is often subjected to additional cycles of selection.

Backcrossing is commonly used to transfer genes for highly heritable traits into a desirable homozygous cultivar or inbred line. The term "backcrossing" refers to the repeated crossing of hybrid progeny back to one of the parental plants, referred to as the recurrent parent. The plant that serves as the source of the transferred trait is called the donor parent. After the initial cross, individuals possessing the transferred trait are selected and repeatedly crossed to the recurrent parent. The resulting plant is expected to have the attributes of the recurrent parent along with the trait transferred from the donor parent.

Transformation Methods

As is noted above, the present invention provides plants and seeds of rice cultivar UADA1701084 in which additional traits have been transferred. While such traits may be selected for using traditional breeding methods, they may also be introduced as transgenes. "Transgenes" include both foreign genes and additional or modified versions of native genes. Plants can be genetically engineered to have a wide variety of traits of agronomic interest including, without limitation, male sterility, waxy starch, herbicide resistance, resistance for bacterial, fungal, or viral disease, insect resistance, male fertility, enhanced nutritional quality, industrial usage, yield stability, and yield enhancement. Many examples of genes that confer such traits have been described in the literature and are well known in the art. For example, the transgene may confer resistance to an herbicide selected from the group consisting of: glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors, and benzonitrile.

Transgenes are typically introduced in the form of an expression vector. As used herein, an "expression vector" is DNA comprising a gene operatively linked to a regulatory element (e.g., a promoter). The expression vector may contain one or more such gene/regulatory element combinations. The expression vector may also include additional sequences, such as a signal sequence or a tag, that modify the protein produced by the transgene. The vector may be a plasmid, and can be used alone or in combination with other plasmids.

Expression vectors include at least one genetic marker operably linked to a regulatory element (e.g., a promoter) that allows transformed cells containing the vector to be recovered by selection. In some embodiments, negative selection (i.e., inhibiting growth of cells that do not contain the selectable marker gene) it utilized. Negative selection markers include, for example, genes that result in detoxification of a chemical agent (e.g., an antibiotic or an herbicide) and genes that result in insensitivity to an inhibitor. Exemplary negative selection genes include neomycin phosphotransferase II (nptII), hygromycin phosphotransferase, gentamycin acetyl transferase, streptomycin phosphotransferase, and aminoglycoside-3'-adenyl transferase. In other embodiments, positive selection (i.e., screening for the product encoded by a reporter gene) is utilized. Exemplary reporter genes include β-glucuronidase, β-galactosidase, luciferase, chloramphenicol acetyltransferase, and Green Fluorescent Protein (GFP).

Transgene expression is typically driven by operably linking the transgene to a promoter within the expression vector. However, other regulatory elements may also be used to drive expression, either alone or in combination with a promoter. As used herein, a "promoter" is a region of DNA upstream of a transcription start site that is involved in recognition and binding of RNA polymerase for transcription initiation. Any class of promoter may be selected to drive the expression of a transgene. For example, the promoter may be "tissue-specific", "cell type-specific", "inducible", or "constitutive". Those of skill in the art know how to select a suitable promoter based the particular circumstances and genetic engineering goals.

Methods for producing transgenic plants are well known in the art. General descriptions of plant expression vectors, reporter genes, and transformation protocols can be found in Gruber, et al., "Vectors for Plant Transformation", in *Methods in Plant Molecular Biology & Biotechnology* in Glich, et al., (Eds. pp. 89-119, CRC Press, 1993). General methods of culturing plant tissues are provided for example by Maki, et al., "Procedures for Introducing Foreign DNA into Plants" in *Methods in Plant Molecular Biology & Biotechnology*, Glich, et al., (Eds. pp. 67-88 CRC Press, 1993); and by Phillips, et al., "Cell-Tissue Culture and In-Vitro Manipulation" in *Corn & Corn Improvement,* 3rd Edition; Sprague, et al., (Eds. pp. 345-387 American Society of Agronomy Inc., 1988). Methods of introducing expression vectors into plant tissue include direct gene transfer methods, such as microprojectile-mediated delivery, DNA injection, and electroporation, as well as the direct infection or co-cultivation of plant cells with *Agrobacterium tumefaciens*, described for example by Horsch et al., *Science,* 227:1229 (1985). Descriptions of *Agrobacterium* vector systems and methods for *Agrobacterium*-mediated gene transfer are provided by Gruber, et al., supra.

REFERENCES

Moldenhauer, K. A. K., J. W. Gibbons, F. N. Lee, J. L. Bernhardt, C. E. Wilson, R. D. Cartwright, M. M. Anders, R. J. Norman, N. A. Slaton, M. M. Blocker, A. C. Tolbert, K. Taylor and J. M. Bulloch. 2007. Registration of >Francis=rice. Crop Sci. 47:443-444

Moldenhauer, K. A. K., J. W. Gibbons, F. N. Lee, J. L. Bernhardt, C. E. Wilson, Jr., R. D. Cartwright, R. J. Norman, M. M. Blocker, D. K. Ahrent, A. M. Stivers, V. A. Boyett, J. M Bulloch, and E. Castaneda. 2010. >Roy J=, high yielding stiff-strawed, long-grain rice variety. In R. J. Norman, and K. A. K. Moldenhauer (eds.) Rice Research Studies 2009. University of Arkansas Agricultural Experiment Station Research Series 581. pp. 53-59

Webb, B. D., C. N. Bollich, H. L. Carnahan, K. A. Kuenzel., and K. S. McKenize. 1985. Utilization characteristics and qualities of United States rice. p. 25-35. In: Rice grain quality and marketing. IRRI, Manila, Philippines

DEPOSIT INFORMATION

A deposit of the University of Arkansas Division of Agriculture Rice Research and Extension Center proprietary rice cultivar UADA1701084 disclosed above and recited in the appended claims has been made with the American Type Culture Collection (ATCC), 10801 University Boulevard, Manassas, Va. 20110. The date of deposit was Jan. 4, 2021. The deposit of 2,500 seeds was taken from the same deposit maintained by the University of Arkansas Division of Agriculture Rice Research and Extension Center (2900 Hwy 130 E., Stuttgart, Ark. 72160) since prior to the filing date of this application. All restrictions will be irrevocably removed upon granting of a patent, and the deposit is intended to meet all of the requirements of 37 C.F.R. §§ 1.801-1.809. The ATCC Accession Number is PTA-126948. The deposit will be maintained in the depository for a period of thirty years, or five years after the last request, or for the enforceable life of the patent, whichever is longer, and will be replaced as necessary during that period.

What is claimed is:

1. A rice seed of the cultivar 'UADA1701084,' a representative sample of seed of said cultivar having been deposited under ATCC Accession No. PTA-126948.

2. A rice plant, or a part thereof, produced by growing the seed of claim 1.

3. A rice plant, or a part thereof, having all of the physiological and morphological characteristics of the rice plant of claim 2.

4. Pollen or an ovule of the plant of claim 2.

5. A method for producing rice plants, said method comprising planting a plurality of rice seeds as recited in claim 1 under conditions favorable for the growth of rice plants.

6. The method of claim 5, further comprising the step of producing rice seed from the resulting rice plants.

7. A rice seed produced by the method of claim 6.

8. A tissue culture of regenerable cells or protoplasts produced from the rice plant of claim 2.

9. The tissue culture of claim 8, wherein said cells or protoplasts are produced from a tissue selected from the group consisting of embryos, meristematic cells, pollen, leaves, anthers, roots, root tips, pistils, anthers, cotyledon, hypocotyl, panicles, flowers, seeds, and stems.

10. A rice plant regenerated from the tissue culture of claim 8, said rice plant having all of the morphological and physiological characteristics of 'UADA1701084'.

11. A method for producing an $F_1$ hybrid rice plant, said method comprising crossing a first parent rice plant with a second parent rice plant, wherein the first parent rice plant or the second patent rice plant is the rice plant of claim 2.

12. The method of claim 11, further comprising the step of producing rice seed from the resulting rice plant.

13. The method of claim 11, wherein the second parent rice plant is transgenic.

14. A method comprising transforming the rice plant of claim 2 or cell thereof with a transgene, wherein the transgene confers at least one trait selected from the group consisting of: herbicide resistance; insect resistance; resistance to bacterial, fungal, or viral disease; modified fatty acid metabolism; modified carbohydrate metabolism; and male sterility.

15. A rice plant or cell thereof produced by the method of claim 14.

16. An herbicide resistant rice plant produced by the method of claim 14, wherein the gene confers resistance to a herbicide selected from the group consisting of glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors and benzonitrile.

17. A method of introducing a desired trait into rice cultivar 'UADA1701084,' said method comprising the steps of:
(a) crossing plants as recited in claim 2 with plants of another rice line expressing the desired trait, to produce progeny plants;
(b) selecting progeny plants that express the desired trait, to produce selected progeny plants;
(c) crossing the selected progeny plants with plants from the 'UADA1701084 parental line to produce new progeny plants;
(d) selecting new progeny plants that express the desired trait; and
(e) repeating steps (c) and (d) three or more times in succession to produce selected higher generation backcross progeny plants that express the desired trait.

18. The method of claim 17, additionally comprising the step of planting a plurality of rice seed produced by selecting higher generation backcross progeny plants under conditions favorable for the growth of rice plants and optionally comprising the step of producing rice seed from the resulting rice plants.

* * * * *